United States Patent [19]

Kiso et al.

[11] Patent Number: 4,460,709

[45] Date of Patent: Jul. 17, 1984

[54] PROCESS FOR PRODUCING OXYGEN-CONTAINING ORGANIC COMPOUNDS

[75] Inventors: Yoshihisa Kiso, Iwakuni; Kenji Saeki, Ohtake, both of Japan

[73] Assignee: Agency of Industrial Science & Technology, Tokyo, Japan

[21] Appl. No.: 406,724

[22] Filed: Aug. 9, 1982

[30] Foreign Application Priority Data

Aug. 13, 1981 [JP] Japan ................................ 56-125928

[51] Int. Cl.$^3$ .............................................. C07C 27/06
[52] U.S. Cl. ...................................... 518/700; 518/715
[58] Field of Search ................................. 518/700, 715

[56] References Cited

U.S. PATENT DOCUMENTS 4,170,605  10/1979  Williamson et al. .

FOREIGN PATENT DOCUMENTS 0013008  7/1980  European Pat. Off. ............ 518/700
55-115834  9/1980  Japan .
56-123925  9/1981  Japan .
57-82327  5/1982  Japan .
57-82328  5/1982  Japan .

OTHER PUBLICATIONS

Dombek, J. Am. Chem. Soc., 1980, 102, 6855–6857.
Deluzarchi, Erdoel und Kohle Erdgas–Petrochemi., 32, 7, (1979), pp. 313–316.
Fonseca et al., Int. High Press. Conf., (U.S.A.), 6th, pp. 733–738, (1979).

*Primary Examiner*—Howard T. Mars
*Attorney, Agent, or Firm*—Wenderoth, Lind & Ponack

[57] ABSTRACT

A process for producing an oxygen-containing organic compound which comprises reacting carbon monoxide with hydrogen in the presence of a catalyst under heat and pressure, said catalyst comprising (a) a ruthenium compound and (b) an imidazole compound.

13 Claims, No Drawings

PROCESS FOR PRODUCING OXYGEN-CONTAINING ORGANIC COMPOUNDS

This invention relates to a process for producing an oxygen-containing organic compound from carbon monoxide and hydrogen. More specifically, it relates to a process for producing a lower aliphatic oxygen-containing organic compound such as ethylene glycol, methanol and methyl acetate from carbon monoxide and hydrogen.

Conventional methods for producing oxygen-containing organic compounds such as ethylene glycol, methanol and ethanol directly from carbon monoxide and hydrogen involve the use of catalyst systems comprising elements of Group VIII of the periodic table including rhodium. Rhodium-containing catalysts have considerably high activity, but methods involving the use of the rhodium catalysts have the defect that the cost of the rhodium catalysts is high, and after the end of the reaction, the rhodium catalysts become inactive as rhodium metal and cannot be easily recovered for re-use.

Accordingly, the methods using the rhodium catalysts are difficult to employ in a commercial process for producing oxygen-containing organic compounds such as ethylene glycol despite their considerably high catalytic activity.

As other noble metal catalysts, the use of ruthenium catalysts is suggested in Japanese Laid-Open Patent Publications Nos. 115,834/1980, 82327/1982 and 82328/1982, U.S. Pat. No. 4,170,605, J. Am. Chem. Soc., 102, 6855 (1980), Erdoel Kohle Erdgas Petrochem., 32, 313 (1979), and Int. High Pressure Conf. (U.S.A.), 6th (1977), [1], 733–738 (1979). Specifically, U.S. Pat. No. 4,170,605 and Int. High Pressure Conf. (U.S.A.), 6th (1977), [1] 733–738 (1979) disclose a method for selectively producing ethylene glycol from carbon monoxide and hydrogen. Japanese Laid-Open Patent Publications Nos. 115,834/1980 and 82,328/1982 disclose a method for selectively producing methanol, ethanol or ethylene glycol from carbon monoxide and hydrogen in the presence of a solubilized ruthenium-carbonyl complex and a catalyst and a Lewis base, for example amines, pyridines or cyclic amines such as purine, pyrimidine or piperazine as a promoter. Japanese Laid-Open Patent Publication No. 123,925/1981 discloses a method for selectively producing ethylene glycol from carbon monoxide and hydrogen in the presence of a ruthenium compound and a compound of another element of Group VIII such as rhodium as a catalyst, and also discloses a method in which a compound, such as a halide or carboxylate salt, of an alkali metal or an alkaline earth metal, or a nitrogen-containing cation or base such as an ammonium salt, an iminium salt or a pyridine is used as a promoter.

The aforesaid methods using ruthenium catalysts are economically advantageous because the cost of the catalysts is low, but the activity of the ruthenium catalysts is lower, for example in ethylene glycol formation, than the rhodium catalysts. According to these methods, the yield of an oxygen-containing organic compound such as ethylene glycol per gram-atom of ruthenium in the ruthenium catalysts is not sufficient under low pressure conditions, for example under 300 kg/cm$^2 \cdot G$ or below.

It is an object of this invention to provide a novel process for producing an oxygen-containing organic compound such as ethylene glycol directly from carbon monoxide and hydrogen in the presence of a specified catalyst system.

Another object of this invention is to provide a process for producing an oxygen-containing organic compound directly in high yields from carbon monoxide and hydrogen.

Still another object of this invention is to provide a process for producing an oxygen-containing organic compound in high yields directly from carbon monoxide and hydroxide using a catalyst system which exhibits excellent activity even under relatively low pressures of, for example about 300 kg/cm$^2 \cdot G$ to about 1 kg/cm$^2 \cdot G$.

Further objects and advantages of this invention will become apparent from the following description.

These objects and advantages are achieved in accordance with this invention by a process for producing an oxygen-containing organic compound which comprises reacting carbon monoxide and hydrogen under heat and pressure in the presence of a catalyst, said catalyst comprising (a) a ruthenium compound and (b) an imidazole.

The catalyst used in the process of this invention is a catalyst comprising (a) a ruthenium compound and (b) an imidazole. This catalyst has not been known heretofore, and has the advantage of giving an oxygen-containing organic compound in a high yield with excellent activity.

There is no particular restriction on the ruthenium compound used in this invention, and any ruthenium compound may be used. For example, the ruthenium compounds disclosed as catalysts in the specifications of the above-cited Japanese Laid-Open Patent Publications Nos. 115,834/1980, 82,327/1982, 82,328/1982, and 123,925/1981 and U.S. Pat. No. 4,170,605 and also be used in the present invention. These specifications are therefore cited herein by reference.

Preferably used in this invention are halogen compounds, carboxylate salts, inorganic acid salts, and oxides of ruthenium, and complexes of ruthenium with various organic or inorganic ligands, such as a ruthenium-carbonyl complex. Specific examples include ruthenium chloride, ruthenium bromide, ruthenium iodide, ruthenium formate, ruthenium acetate, ruthenium nitrate, ruthenium dioxide, ruthenium tetroxide, Ru(acetylacetonate)$_3$, $(C_5H_5)(CH_3)Ru(CO)_2$, $(C_5H_5)_2Ru$, $Ru_3(CO)_{12}$, $Ru(CO)_4^{2-}$, $Ru_6(CO)_{18}^{2-}$, $H_2Ru_4(CO)_{13}$, $H_6Ru_4(CO)_{12}$, and $[Ru(CO)_3CL_2]_2$. A fine powder of ruthenium metal can also be used because it reacts with carbon monoxide in the reaction system of this invention to form a carbonyl complex soluble in the reaction system.

The concentration of the ruthenium compound (a) in the reaction system is not particularly limited. Usually, it is 1 to $10^{-6}$ gram-atom/liter, preferably $2 \times 10^{-1}$ to $10^{-4}$ gram-atom/liter, as the concentration of ruthenium atom in the reaction system.

Various compounds can be used as the imidazole (b), the other ingredient of the catalyst used in this invention. This shows that the imidazole ring moiety of the imidazole compound contributes greatly to the catalytic activity of the catalyst used in this invention.

Preferred imidazoles (b) used in this invention are compounds represented by the following formula

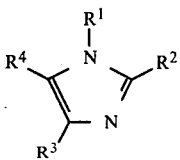

(I)

wherein $R^1$, $R^2$, $R^3$ and $R^4$ are identical or different and each represents a hydrogen atom or a monovalent substituent, or $R^1$ and $R^2$, or $R^3$ and $R^4$, or $R^1$ and $R^4$ may be taken together to form a substituted or unsubstituted hydrocarbon group.

Preferably, the monovalent substituent in formula (I) is substantially non-reactive with the resulting oxygen-containing organic compound under the reaction conditions. Examples of the substituent include halogen atoms such as chlorine, bromine, fluorine and iodine, a hydroxyl group, a carboxyl group, acyl groups such as formyl, acetyl, butyroyl, benzoyl and toluoyl, an amino group, substituted amino groups such as dimethylamino and diethylamino, alkoxy groups such as methoxy and ethoxy, a cyano group, an isocyano group, a nitro group, a silyl group, alkyl-substituted silyl groups such as trimethylsilyl, hydrocarbon groups such as methyl, ethyl, n-propyl, iso-propyl, n-butyl, iso-butyl, tert-butyl, octyl, dodecyl, hexadecyl, cyclohexyl, phenyl and benzyl, and substituted hydrocarbon groups substituted by the aforesaid polar groups, such as hydroxyalkyl, carboxyalkyl and aminoalkyl.

The adjacent substituents, $R^1$ and $R^2$, $R^3$ and $R^4$, or $R^1$ and $R^4$, may together form a substituted or unsubstituted hydrocarbon group. Preferably such a hydrocarbon group has 5 to 7, preferably 5, carbon atoms as ring-members including the two carbon atoms to which they are bonded. In such a hydrocarbon group, one ring-member carbon atom may be substituted by one ring-member nitrogen atom, or by a monovalent substituent. Examples of such a monovalent substituent are the same as those exemplified hereinabove. Preferred imidazoles of formula (I) are unsubstituted imidazole, substituted imidazoles having polar groups as substituents such as hydrocarbon group-substituted imidazoles, hydroxyalkyl group-substituted imidazoles, carboxyalkyl group-substituted imidazoles, aminoalkyl group-substituted imidazoles and polyvinylimidazole, and benzimidazoles.

Among them, the benzimidazoles are especially preferred. The benzimidazoles are compounds represented by the following formula

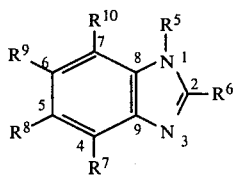

(I')

wherein $R^5$, $R^6$, $R^7$, $R^8$, $R^9$ and $R^{10}$ are identical or different and each represents a hydrogen atom or a monovalent substituent, or $R^6$ and $R^{10}$, $R^5$ and $R^6$, $R^7$ and $R^8$, $R^8$ and $R^9$, or $R^9$ and $R^{10}$ may be taken together to form a substituted or unsubstituted hydrocarbon group.

In formula (I)', the definitions of $R^5$ to $R^{10}$ are the same as those of $R^1$ to $R^4$.

Examples of the imidazoles (b) of formula (I) [including formula (I)'] are imidazole; imidazoles substituted by hydrocarbon groups, such as 1-methylimidazole, 1-ethylimidazole, 1-n-propylimidazole, 1-iso-propylimidazole, 1-butylimidazole, 2-methylimidazole; 2-ethylimidazole, 2-n-propylimidazole, 2-iso-propylimidazole, 4-methylimidazole, 4-ethylimidazole, 3-n-propylimidazole, 4-isopropylimidazole, 4-butylimidazole, 4,5-dimethylimidazole, 4,5-diethylimidazole, 1-methyl-2-ethylimidazole, 1-methyl-4-ethylimidazole, 1-phenylimidazole, 4-phenylimidazole, benzimidazole, 1,2-trimethyleneimidazole, 1,5-trimethyleneimidazole, 4,5-trimethyleneimidazole and 4,5,6,7-tetrahydrobenzimidazole; imidazoles substituted by hydrocarbon groups which are substituted by polar groups, such as 1-hydroxymethylimidazole, 2-hydroxymethylimidazole, 4-hydroxymethylimidazole, 1-(2-hydroxyethyl)imidazole, 2-(2-hydroxyethyl)imidazole, 4-2(hydroxyethyl)imidazole, 1-carboxymethylimidazole, 2-carboxymethylimidazole, 4-carboxymethylimidazole, 1-(2-carboxyethyl)imidazole, 4-(2-carboxyethyl)imidazole, 4-(2-carboxy-2-hydroxyethyl)imidazole, 1-aminomethylimidazole, 4-aminomethylimidazole, 1-(2-aminoethyl)imidazole, 4-(2-aminoethyl)imidazole, 1-(3-aminopropyl)imidazole, 4-(3-aminopropyl)imidazole, 2-(2-imidazolyl)imidazole, 4-(2-pyridyl)imidazole and 2-benzoylimidazole; benzimidazoles such as benzimidazole, 1-methylbenzimidazole, 1-ethylbenzimidazole, 1-n-propylbenzimidazole, 1-iso-propylbenzimidazole, 1-tert-butylbenzimidazole, 1-n-butylbenzimidazole, 1-phenylbenzimidazole, 1-benzylbenzimidazole, 1-cyclohexylbenzimidazole, 1-octylbenzimidazole, 1-dodecylbenzimidazole, 1-hexadecylbenzimidazole, 1-trimethylsilylmethylbenzimidazole, 4-methylbenzimidazole, 5,6-dimethylbenzimidazole, 4,5,6-trimethylbenzimidazole, 1-methyl-5,6-dimethylbenzimidazole, 1-ethyl-5,6-dimethylbenzimidazole, 1-isopropyl-5,6-dimethylbenzimidazole, 5,6-dimethoxybenzimidazole, 4,5-trimethylenebenzimidazole, naphtho[1,2-d]imidazole, naphtho[2,3-d]imidazole, 1-methyl-4-methoxybenzimidazole, 1-methyl-5-methoxybenzimidazole, 1-methyl-5,6-dimethoxybenzimidazole, 1-methyl-5-dimethylaminobenzimidazole, 1-methyl-5-aminobenzimidazole and 1-methyl-5-trimethylsilylbenzimidazole; and azabenzimidazoles such as 4-azabenzimidazole and 1-methyl-4-azabenzimidazole.

One or more imidazoles (b) may be used in this invention. The preferred concentration of the imidazole (b) in the reaction system is $10^{-3}$ to 10 moles per liter of the reaction mixture.

The process of this invention is characterized by using a combination of the ruthenium compound (a) and the imidazole (b) as a catalyst. The imidazole compound (b) can be used in an amount of $10^{-1}$ to $10^7$ moles per gram-atom of ruthenium of the ruthenium compound (a). Generally, it is preferred to use the imidazole in a larger amount than the ruthenium compound, particularly in an amount of 10 to $10^5$ moles per gram-atom of ruthenium of the ruthenium compound (a).

Another catalyst ingredient (promoter) may be used in this invention together with the ruthenium compound (a) and the imidazole (b). Examples of the promoter are compounds of elements selected from elements of Groups VI and VII of the periodic table and elements of Group VIII other than ruthenium. The compounds may, for example, be halogen compounds, carboxylate salts, inorganic acid salts, and oxides of such elements or complexes of such elements with various ligands such as carbon monoxide. Specific examples of these compounds are described in Japanese Laid-Open Patent Publication No. 123,925/1981 cited hereinabove. Other halogen elements or compounds may also be used as promoters in this invention. Specific examples include halogen elements such as iodine, bromine and chlorine, hydrogen halides such as hydrogen iodide, hydrogen bromide, hydrogen chloride and hydrogen fluoride, halides of alkali metals, alkaline earth metals, aluminum or phosphorous quaternary ammonium halides, quaternary phosphonium halides, iminium halides, alkyl halides, and aryl halides.

Specific examples of the halides of alkali metals, alkaline earth metals, aluminum or phosphorus are lithium fluoride, lithium chloride, lithium bromide, lithium iodide, sodium fluoride, sodium chloride, sodium bromide, sodium iodide, potassium fluoride, potassium chloride, potassium bromide, potassium iodide, rubidium chloride, rubidium bromide, rubidium iodide, cesium fluoride, cesium chloride, cesium bromide, cesium iodide, aluminum trichloride, phosphorus trichloride, and phosphorus pentachloride.

Compounds formed by the reaction of various amines with alkyl halides or aryl halides may be used as the quaternary ammonium halides. Specific examples include tetramethylammonium chloride, tetramethylammonium bromide, tetramethylammonium iodide, tetramethylammonium fluoride, tetraethylammonium chloride, tetraethylammonium bromide, tetra-n-propylammonium halides, tetra-n-butylammonium halides, trimethylbenzylammonium halides, triethylbenzylammonium halides, triisopropylbenzyl ammonium halides, pyridinium halides (e.g., N-methylpyridinium halides, 1-methyl-2-hydroxypyridinium halides and methyl-4-dimethylaminopyridinium halides) and imidazolium halides such as methyl-1-methylimidazolium halides and ethyl-1-methylimidazolium halides.

Examples of the quaternary phosphonium halides are tetramethylphosphonium chloride, tetramethylphosphonium iodide, tetramethylphosphonium bromide, tetramethylphosphonium fluoride, tetraethylphosphonium iodide, tetraethylphosphonium bromide, tetraethylphosphonium chloride, tetraethylphosphonium fluoride, tetra-n-propylphosphonium halides, tetra-n-butylphosphonium halides, tetraphenylphosphonium halides, triphenylmethylphosphonium halides, and triphenylethylphosphonium halides.

Examples of the iminium halides are bis(triphenylphosphine)iminium iodide, bis(triphenylphosphine)iminium bromide, and bis(triphenylphosphine)iminium chloride.

Preferred alkyl or aryl halides are $C_{1-20}$ alkyl or aryl halides. Specific examples include methyl iodide, ethyl iodide, ethyl bromide, ethyl chloride, isopropyl iodide, isopropyl bromide, isopropyl chloride, n-butyl iodide, n-butyl bromide and n-butyl fluoride, phenyl iodide, phenyl bromide, benzyl iodide, and benzyl bromide.

The promoter components exemplified hereinabove may be used singly or as a mixture of two or more. When the promoter is a compound of an element of Group VI, VII or VIII (other than ruthenium) of the periodic table, it is preferably used in such a proportion that the ratio of the gram-atoms of the metalic element of the promoter compound to the gram-atoms of ruthenium in the reaction system is from about $10^{-2}$ to about $10^2$, especially from about $10^{-1}$ to about 10.

When the other halogen compound is used, its amount is desirably such that the ratio of the moles of the halogen compound to the gram-atoms of ruthenium in the reaction system is from about $10^{-2}$ to about $10^3$, especially from about $10^{-1}$ to about $10^2$.

The addition of the catalyst to the reaction system in the process of this invention can be effected in various modes. For example, a mixture is prepared from the ruthenium compound (a), the imidazole compound (b) and as required, the promoter and then added to the reaction system. Or at least two compounds of the same component are mixed in advance, and such mixtures are added separately to the reaction system. Or these components may be added separately to the reaction system without mixing.

The ruthenium compound (a) may be diluted with an organic diluent prior to being mixed with the other catalyst components or being added to the reaction system. The imidazole (b) may also be used as an organic diluent for the ruthenium component (b) and the other catalyst components.

The imidazole (b) may be formed in situ in the reaction system, for example, by the method disclosed in Advances in Hetterocyclic Chemistry 12, pages 103-183.

Usually, the reaction in accordance with this invention is carried out in the presence of a solvent. Any organic solvent inert to the reaction may be used for this purpose. Specific examples of the solvent include ethers such as tetrahydrofuran, diethylene glycol dimethyl ether, tetraethylene glycol dimethyl ether (tetraglyme), diethyl ether, diisopropyl ether, dioxane, 1,2-dimethoxybenzene and 18-crown-6; esters such as methyl acetate, ethyl acetate, butyl acetate, ethylene glycol diacetate, diethylene glycol diacetate, $\gamma$-butyrolactone, dimethyl-$\gamma$-butyrolactone and $\delta$-valerolactone; sulfones such as sulfolane and dimethylsulfone; sulfoxides such as dimethyl sulfoxide and diethyl sulfoxide; amides such as N,N-dimethylformamide, N,N-diethylformamide, N,N-dimethylacetamide, N-methylpyrrolidone, N-ethylpyrrolidone, N-isopropylpyrrolidone, N-propylpyrrolidone, N-butylpyrrolidone, N-octylpyrrolidone, N-cyclohexylpyrrolidone, N-benzylpyrrolidone, polyvinylpyrrolidone and N-methyl-2-pyridone; phosphoric acid triamides such as hexamethylphosphoric triamide and hexaethylphosphoric triamide; substituted ureas such as N,N,N',N'-tetramethylurea and 1,3-dimethyl-2-imidazolidinone; alcohols such as methanol, ethanol, 2-methoxyethanol, ethylene glycol, diethylene glycol and triethylene glycol; carboxylic acids such as acetic acid, propionic acid and benzoic acid; phenols such as phenol and resorcinol; amines such as trimethylamine and triethylamine; pyridines such as pyridine and 2-hydroxypyridine; nitriles such as acetonitrile and benzonitrile; ketones such as acetone and diphenyl ketone; hydrocarbons such as hexane, heptane, hexene, cyclohexane, naphtha, and kerosene; and aromatic hydrocarbons such as benzene, toluene and xylene. The use of aprotic dipolar solvents, such as the esters, polyethers, sulfones and amides, is preferred because it increases the rate of the reaction. It is also possible to use the imidazole (b) in excess to make it serve also as a reaction solvent.

The proportions of carbon monoxide and hydrogen gas to be fed to the reaction system in the process of this invention are such that the mole ratio of carbon monoxide to hydrogen is usually from 20 to 0.05, preferably from 5 to 0.2.

The reaction in the process of this invention is carried out under heat and pressure. The reaction pressure is usually from 2,000 to 1 kg/cm$^2$-G, preferably from 1,000 to 50 kg/cm²-G. Generally, the higher the reaction pressure, the higher the rate of the reaction. The process of this invention is characterized, however, by the fact that even at relatively low pressures, oxygen-containing organic compounds typified by alkanepolyols are formed in high yields. The reaction temperature is usually from 50° to 350° C., preferably from 150° to 300° C. The time required for the reaction is usually from 0.1 to 20 hours, preferably from 0.5 to 10 hours. Usually, the reaction is carried out with stirring.

To isolate the resulting oxygen-containing organic compound from the reaction mixture, the reaction mixture is treated in a customary manner, for example by distillation or extraction.

In particular, the process of this invention can afford lower aliphatic oxygen-containing compounds, for example alcohols having 1 to 3 carbon atoms, carboxylic acids having 1 to 3 carbon atoms, and esters between these alcohols and carboxylic acids, such as methanol, ethanol, ethylene glycol, 1,2-propanediol, glycerol, formic acid, acetic acid, propionic acid, methyl acetate, methyl formate, ethylene glycol monoformate and ethylene glycol monoacetate.

The process of this invention should be evaluated especially highly as a technique of producing ethylene glycol.

The following examples illustrate the process of this invention more specifically.

The products were analyzed by a gas chromatograph utilizing a 1.1 meter glass column packed with Chromosorb 102 and deposited thereon 10% of PEG 20M-TPA and the temperature of column was set at 80° C. for 4 minutes and then increased from 80° C. to 240° C. at a rate of 8° C. per minute. Then, volatile components are detected by the TCD method.

EXAMPLE 1

The inside of a 60 ml autoclave made of Hastelloy C was purged with argon. The autoclave was charged with 0.4 milligram-atom of $Ru_3(CO)_{12}$, 40 millimoles of imidazole and 10 ml of N-methylpyrrolidone (NMP for short) and then closed. A gaseous mixture of carbon monoxide and hydrogen in a mole ratio of 1:1 was introduced into the autoclave through a gas introducing tube, and reacted for 2 hours at a pressure of 550 kg/cm² and a temperature of 240° C.

After the reaction, the reaction mixture was cooled to room temperature, and after discharging the excess gas, withdrawn.

The reaction mixture was then quantitatively determined by gas chromatography. The results are shown in Table 1. In the tables, the symbol "—" shows a very small amount although the amount was not accurately determined.

EXAMPLES 2 TO 62

Example 1 was followed except that the catalyst and the solvent were changed as shown in Table 1, and in some Examples, the reaction conditions were changed as shown below. The results are also shown in Table 1.

In Examples 11 and 27, the reaction times were 4 hours, and 2.5 hours, respectively. In Examples 21 and 22, the reaction temperature was 260° C. In Example 23, the reaction temperature was 270° C. In Example 49, 15 ml of NMP (solvent) was used. In Examples 41 and 42, tetraglyme was used in an amount of 5 ml. In Example 20, 0.5 millimole of acetic acid was formed in addition to the products shown in Table 1. In Example 41, 1.6 millimoles of acetic acid, 0.8 millimole of glycerol, 0.1 millimole of ethylene glycol monochloroformate and 1.4 millimoles of ethylene glycol monoacetate were formed in addition to the products shown in Table 1.

TABLE 1

| Example | Catalyst $Ru_3(CO)_{12}$ (mg-atom) | Imidazole compound (millimoles) | Solvent | Methanol | Methyl formate | Ethanol | Methyl acetate | Ethylene glycol | 1,2-Propanediol |
|---|---|---|---|---|---|---|---|---|---|
| 1 | 0.4 | Imidazole (40) | NMP | 61.8 | 2.4 | 0.3 | 0 | 4.0 | 0.4 |
| 2 | 0.1 | Imidazole (10) | NMP | 35.2 | 1.0 | 0.2 | 0 | 1.1 | 0.1 |
| 3 | 0.1 | 1-Methylimidazole (10) | NMP | 10.8 | 0.3 | 0.1 | 0 | 1.1 | 0.1 |
| 4 | 0.1 | 1-Methylimidazole (50) | NMP | 16.2 | 0.5 | 0.5 | 0 | 3.4 | 0 |
| 5 | 0.1 | 1-Ethylimidazole (10) | NMP | 19.1 | 0.4 | 0.2 | 0.1 | 2.2 | 0.4 |
| 6 | 0.1 | 1-Trimethylsilylimidazole (10) | NMP | 26.1 | 1.2 | 0.1 | 0 | 1.0 | 0 |
| 7 | 0.1 | 2-Methylimidazole (10) | NMP | 32.2 | 0.8 | 0.1 | 0.1 | 1.4 | 0.3 |
| 8 | 0.1 | 2-Ethylimidazole (10) | NMP | 28.0 | 0.5 | 0.1 | — | 1.0 | 0.1 |
| 9 | 0.1 | 2-n-Dodecylimidazole (10) | NMP | 26.6 | 0.5 | 0.1 | — | 0.8 | 0.1 |
| 10 | 0.1 | 4-Methylimidazole (10) | NMP | 37.5 | 1.0 | 0.1 | 0.1 | 1.7 | 0.2 |
| 11 | 0.1 | 4-Nitroimidazole (10) | NMP | 0.1 | 0 | 0 | 0 | 0.01 | 0 |
| 12 | 0.1 | 1,2-Dimethylimidazole (10) | NMP | 13.6 | 0.2 | 0.1 | — | 1.1 | 0.2 |
| 13 | 0.1 | 4,5-Diphenylimidazole (10) | NMP | 11.2 | 0.4 | 0 | 0.1 | 0.1 | 0 |
| 14 | 0.1 | 2-Ethyl-4-methylimidazole (10) | NMP | 24.1 | 0.3 | — | — | 0.9 | 0.1 |
| 15 | 0.1 | 2-[2-(4,5-Dimethylimidazolyl]-4,5-dimethylimidazole (5) | NMP | 0.6 | — | — | — | 0.1 | 0 |

TABLE 1-continued

| Example | Catalyst Ru₃(CO)₁₂ (mg-atom) | Imidazole compound (millimoles) | | Solvent | Products (millimoles) Methanol | Methyl formate | Ethanol | Methyl acetate | Ethylene glycol | 1,2-Propanediol |
|---|---|---|---|---|---|---|---|---|---|---|
| 16 | 0.1 | Benzimidazole | (10) | NMP | 13.5 | 0.5 | 0.2 | 0.1 | 3.9 | 0.5 |
| 17 | 0.1 | Benzimidazole | (50) | NMP | 28.2 | 0.7 | 0.7 | 0.9 | 9.7 | 1.0 |
| 18 | 0.1 | Benzimidazole | (100) | NMP | 28.0 | 0.5 | 0.3 | 0.6 | 6.2 | 0.2 |
| 19 | 0.05 | Benzimidazole | (25) | NMP | 15.7 | 0.5 | 0.3 | 0.2 | 4.8 | 0.5 |
| 20 | 0.05 | Benzimidazole | (50) | NMP | 22.7 | 0.5 | 0.5 | 0.6 | 7.7 | 0.7 |
| 21 | 0.1 | Benzimidazole | (10) | NMP | 23.1 | 0.8 | 0.5 | 0.4 | 6.2 | 0.7 |
| 22 | 0.1 | Benzimidazole | (50) | NMP | 32.1 | 0.9 | 1.4 | 3.0 | 13.2 | 1.2 |
| 23 | 0.1 | Benzimidazole | (50) | NMP | 27.9 | 0.7 | 1.5 | 3.5 | 11.2 | 1.1 |
| 24 | 0.1 | Benzimidazole | (10) | Tetraglyme | 12.2 | 1.1 | 0.2 | 0.1 | 4.9 | 0.3 |
| 25 | 0.1 | Benzimidazole | (10) | 1,2-Propanediol | 10.3 | 0.7 | 0.9 | 0.2 | 2.3 | 0 |
| 26 | 0.1 | Benzimidazole | (10) | Diethylene glycol | 7.9 | 0.6 | 0.2 | 0.1 | 2.6 | 0.2 |
| 27 | 0.1 | Benzimidazole | (10) | Ethanol | 10.7 | 0.8 | — | 0 | 2.7 | 0.3 |
| 28 | 0.1 | Benzimidazole | (10) | Polyethylene glycol 600 | 7.3 | 0.4 | 0.1 | 0.1 | 3.3 | 0.1 |
| 29 | 0.1 | Benzimidazole | (10) | Diethylene glycol monoethyl ether | 9.2 | 0.9 | 0.3 | 0 | 3.4 | 0.4 |
| 30 | 0.1 | Benzimidazole | (10) | 18-crown-6 | 14.7 | 1.0 | 0.4 | 0.4 | 5.7 | 0.4 |
| 31 | 0.1 | Benzimidazole | (10) | γ-Butyrolactone | 6.7 | 0.2 | — | 0 | 0.5 | 0 |
| 32 | 0.1 | Benzimidazole | (10) | Diphenyl ether | 8.8 | 0.8 | 0.1 | 0.1 | 3.4 | 0.1 |
| 33 | 0.1 | Benzimidazole | (10) | Dimethylimidazolidinone | 13.9 | 0.7 | 0.3 | 0.1 | 5.0 | 0.5 |
| 34 | 0.1 | Benzimidazole | (10) | N—ethyl-pyrrolidone | 15.8 | 0.7 | 0.5 | 0.2 | 4.5 | 0.6 |
| 35 | 0.1 | Benzimidazole | (10) | Sulfolane | 7.2 | 0.3 | 0.2 | — | 2.2 | 0.1 |
| 36 | 0.1 | Benzimidazole | (10) | Benzene | 11.9 | 0.8 | 0.1 | 0.1 | 2.3 | 0 |
| 37 | 0.1 | Benzimidazole | (10) | N—Benzylpyrrolidone | 11.9 | 0.7 | 0.4 | — | 4.8 | 0.6 |
| 38 | 0.1 | Benzimidazole | (10) | N,N—Diethylaniline | 8.6 | 0.8 | 0.1 | 0 | 2.3 | 0.1 |
| 39 | 0.1 | Benzimidazole | (10) | Pyridine | 19.5 | 0.6 | 0.1 | 0 | 3.8 | 0 |
| 40 | 0.1 | 1-Methylbenzimidazole | (10) | Tetraglyme | 3.0 | 0.3 | 0.2 | 0 | 3.7 | 0.1 |
| 41 | 0.05 | 1-Methylbenzimidazole | (50) | Tetraglyme | 5.0 | 0.2 | 0.8 | 0.6 | 4.9 | 0.4 |
| 42 | 0.05 | 1-Methylbenzimidazole | (25) | Tetraglyme | 3.1 | 0.2 | 0.5 | 0.3 | 3.7 | 0.2 |
| 43 | 0.1 | 1-Methylbenzimidazole | (5) | Tetraglyme | 1.7 | 0.2 | 0 | 0 | 1.6 | 0 |
| 44 | 0.1 | 1-Methylbenzimidazole | (2) | Tetraglyme | 0.7 | 0.1 | 0 | 0 | 0.6 | 0 |
| 45 | 0.1 | 1-Methylbenzimidazole | (0.5) | Tetraglyme | 0.3 | 0 | 0 | 0 | 0.1 | 0 |
| 46 | 0.1 | 1-Methylbenzimidazole | (10) | NMP | 4.5 | 0.2 | 0.3 | 0 | 3.3 | 0.2 |
| 47 | 0.1 | 1-Ethylbenzimidazole | (10) | Tetraglyme | 3.7 | 0.4 | 0.2 | 0 | 4.9 | 0.2 |
| 48 | 0.05 | 1-Ethylbenzimidazole | (45) | Tetraglyme | 5.1 | 0.2 | 0.7 | 0.4 | 7.8 | 0.6 |
| 49 | 0.1 | 1-iso-propyl-benzimidazole | (10) | Tetraglyme | 7.5 | 0.6 | 0.2 | 0.1 | 4.6 | 0.3 |
| 50 | 0.1 | 2-Hydroxybenzimidazole | (10) | NMP | 1.4 | — | — | 0 | 0 | 0 |
| 51 | 0.1 | 2-Methylbenzimidazole | (10) | NMP | 11.9 | 0.3 | — | — | 0.9 | 0.1 |
| 52 | 0.1 | 2-Aminobenzimidazole | (10) | NMP | 1.5 | 0.2 | 0.1 | 0 | 0.3 | 0 |
| 53 | 0.1 | 6-Nitrobenzimidazole | (10) | NMP | 19.8 | 0.7 | — | 0.2 | 0.7 | 0.1 |
| 54 | 0.1 | 1-Ethyl-2-Methylbenzimidazole | (10) | NMP | 5.9 | 0.1 | — | — | 0.8 | — |
| 55 | 0.1 | 5,6-Dimethyl-benzimidazole | (10) | NMP | 20.2 | 0.7 | 0.3 | 0.2 | 5.4 | 0.5 |

TABLE 1-continued

| Example | Catalyst Ru₃(CO)₁₂ (mg-atom) | Imidazole compound (millimoles) | | Solvent | Products (millimoles) Methanol | Methyl formate | Ethanol | Methyl acetate | Ethylene glycol | 1,2-Propanediol |
|---|---|---|---|---|---|---|---|---|---|---|
| 56 | 0.05 | 5,6-Dimethyl-benzimidazole | (50) | NMP | 21.2 | 0.4 | 0.6 | 0.5 | 7.1 | 0.7 |
| 57 | 0.1 | 5,6-Dimethyl-benzimidazole | (10) | N—benzyl-pyrrolidone | 15.4 | 0.7 | 0.5 | 0.3 | 6.3 | 0.6 |
| 58 | 0.1 | 5,6-Dimethyl-benzimidazole | (10) | Tetraglyme | 13.8 | 1.1 | 0.2 | 0.1 | 6.4 | 0.4 |
| 59 | 0.1 | 2,5,6-Tri-methylbenz-imidazole | (10) | NMR | 21.2 | 0.5 | 0.1 | — | 1.1 | 0.1 |
| 60 | 0.1 | 1-iso-Propyl-5,6-dimethyl-benzimidazole | (10) | Tetraglyme | 8.9 | 0.8 | 0.2 | 0.1 | 7.4 | 0.5 |
| 61 | 0.02 | 1-iso-Propyl-5,6-dimethyl-benzimidazole | (20) | Tetraglyme | 3.3 | 0.2 | 0.2 | 0.1 | 2.4 | 0.2 |
| 62 | 0.1 | 4-Azabenz-imidazole | (10) | NMP | 32.0 | 0.6 | 0.1 | 0 | 0.3 | — |

EXAMPLES 63 TO 73

Example 40 was followed except that the $H_2/CO$ mole ratio, the reaction pressure and the reaction temperature were changed as indicated in Table 2. The results are shown in Table 3.

TABLE 2

| Example | $H_2/CO$ (mole ratio) | Reaction conditions Pressure (kg/cm²) | Temperature (°C.) |
|---|---|---|---|
| 63 | 1.0 | 420 | 240 |
| 64 | 1.0 | 330 | 240 |
| 65 | 1.0 | 260 | 240 |
| 66 | 1.0 | 220 | 240 |
| 67 | 1.0 | 120 | 240 |
| 68 | 1.0 | 550 | 276 |
| 69 | 1.0 | 550 | 260 |
| 70 | 1.0 | 550 | 220 |
| 71 | 1.0 | 550 | 200 |
| 72 | 1.9 | 550 | 240 |
| 73 | 1.9 | 550 | 277 |

TABLE 3

| Example | Product (millimoles) Methanol | Methyl formate | Ethanol | Methyl acetate | Ethylene glycol | 1,2-Propanediol |
|---|---|---|---|---|---|---|
| 63 | 3.0 | 0.2 | 0.1 | 0 | 3.5 | — |
| 64 | 2.9 | 0.2 | 0.1 | 0 | 3.3 | — |
| 65 | 3.1 | 0.2 | — | 0 | 2.8 | — |
| 66 | 3.0 | 0.1 | — | 0 | 1.9 | 0.1 |
| 67 | 1.9 | 0.1 | — | 0 | 0.3 | — |
| 68 | 10.2 | 0.6 | 0.8 | 0.6 | 12.2 | 0.4 |
| 69 | 4.7 | 0.3 | 0.4 | 0.1 | 6.1 | 0.2 |
| 70 | 1.7 | 0.2 | — | 0 | 1.8 | — |
| 71 | 0.8 | — | — | 0 | 0.5 | — |
| 72 | 7.2 | 0.5 | 0.1 | 0 | 9.5 | 0.1 |
| 73 | 39.1 | 1.2 | 0.5 | 0.8 | 31.8 | 0.1 |

EXAMPLES 74 TO 76

Example 16 was followed except that 0.1 milligram-atom of each of the Ru compounds shown in Table 4 was used instead of $Ru_3(CO)_{12}$. The results are also shown in Table 4.

TABLE 4

| Example | Ru compound | Products (millimoles) Methanol | Methyl formate | Ethanol | Methyl acetate | Ethylene glycol | 1,2-Propanediol |
|---|---|---|---|---|---|---|---|
| 74 | $RuCl_3 \cdot 3H_2O$ | 11.3 | 0.3 | 0.6 | 0.2 | 2.2 | 0.3 |
| 75 | $RuO_2$ | 11.7 | 0.4 | 0.2 | 0.2 | 2.9 | 0.4 |
| 76 | Ru(acetyl-acetonate)₂ | 3.9 | 0.2 | 0 | — | 1.6 | 0.2 |

EXAMPLES 77 TO 79

The same autoclave as used in Example 1 was charged with 0.1 milligram-atom of $Ru_3(CO)_{12}$ and each of the imidazole compounds shown in Table 5 in the amounts indicated, and a gaseous mixture of carbon monoxide and hydrogen in a molar ratio of 1:1 was introduced into the autoclave and reacted at a temperature of 240° C. and a pressure of 550 kg/cm²-G for 2 hours.

The results are also shown in Table 5.

TABLE 5

| Example | Imidazole compound (ml) | Products (millimoles) Methanol | Methyl formate | Ethanol | Methyl acetate | Ethylene glycol | 1,2-Propanediol |
|---|---|---|---|---|---|---|---|
| 77 | 1-Methylimidazole (7.5) | 7.6 | 0.3 | 0.5 | 0 | 2.6 | 0 |
| 78 | Benzimidazole (10) | 7.7 | 0.1 | 0.1 | 0.1 | 1.6 | — |
| 79 | 1-Methylbenzimidazole (10) | 10.91 | 0.3 | 0.9 | 2.6 | 7.5 | 0.4 |

EXAMPLES 80 TO 93

The same autoclave as used in Example 1 was charged with each of the catalysts shown in Table 6 in the indicated amounts and 10 ml of each of the solvents shown in Table 6. A mixture of carbon monoxide and hydrogen in a mole ratio of 1:1 was introduced into the autoclave and reacted under the conditions shown in Table 6. The results are shown in Table 7.

For example, in Example 83, the amount of $CO_2$ formed decreased to 40% of that formed without adding $W(CO)_6$.

TABLE 7

| Example | Products (millimoles) | | | | | |
|---|---|---|---|---|---|---|
| | Methanol | Methyl formate | Ethanol | Methyl acetate | Ethylene glycol | 1,2-Propanediol |
| 80 | 9.3 | 0.9 | 0.2 | — | 6.4 | 0.5 |
| 81 | 16.9 | 1.7 | 0.3 | 0.2 | 6.4 | 0.5 |
| 82 | 15.2 | 1.6 | 0.3 | 0.2 | 6.4 | 0.6 |
| 83 | 14.4 | 1.5 | 0.3 | 0.2 | 6.0 | 0.6 |
| 84 | 36.3 | 1.6 | 0.1 | — | 2.7 | 0.2 |
| 85 | 14.0 | 0.1 | 4.1 | 0.4 | 6.5 | 1.2 |
| 86 | 10.2 | 0.1 | 1.4 | — | 4.9 | 0.8 |
| 87 | 9.8 | 0.1 | 0.9 | — | 4.8 | 0.6 |
| 88 | 10.3 | 0.1 | 1.0 | — | 4.7 | 0.5 |
| 89 | 7.3 | 0.1 | 0.5 | — | 3.8 | 0.4 |
| 90 | 9.7 | 0.1 | 3.3 | — | 6.2 | 0.9 |

TABLE 6

| Example | Catalyst (mg-atom for metal compounds, and millimoles for the others) | | | | | Reaction conditions | | |
|---|---|---|---|---|---|---|---|---|
| | $Ru_3(CO)_{12}$ (mg-atom) | Imidazole compound (millimoles) | Additive | Additive | Solvent | Temperature (°C.) | Time (hr) | Pressure ($kg/cm^2$) |
| 80 | 0.075 | Benzimidazole (10) | $Rh(CO)_2$ acetylacetonate (0.024) | — | Tetraglyme | 240 | 2 | 550 |
| 81 | 0.10 | Benzimidazole (10) | $Re_2(CO)_{10}$ (0.10) | — | Tetraglyme | 240 | 2 | 550 |
| 82 | 0.10 | Benzimidazole (10) | $Mo(CO)_6$ (0.10) | — | Tetraglyme | 240 | 2 | 550 |
| 83 | 0.10 | Benzimidazole (10) | $W(CO)_6$ (0.10) | — | Tetraglyme | 240 | 2 | 550 |
| 84 | 0.30 | Imidazole (40) | $Rh(CO)_2$ acetylacetonate (0.10) | — | NMP | 200 | 2 | 550 |
| 85 | 0.10 | 1-Methylbenzimidazole (7) | 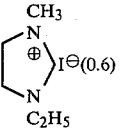 (0.6) | — | NMP | 240 | 2 | 550 |
| 86 | 0.10 | 1-Methylbenzimidazole (10) | $LiI \cdot 3H_2O$ (0.7) | — | NMP | 240 | 2 | 550 |
| 87 | 0.10 | 1-Methylbenzimidazole (10) | $KI$ (0.7) | — | NMP | 240 | 2 | 550 |
| 88 | 0.10 | 1-Methylbenzimidazole (10) | $CsI$ (0.6) | — | NMP | 240 | 2 | 550 |
| 89 | 0.10 | 1-Methylbenzimidazole (10) | $CsCl$ (0.7) | — | NMP | 240 | 2 | 550 |
| 90 | 0.10 | 1-Methylbenzimidazole (10) | 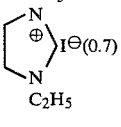 (0.7) | — | NMP | 240 | 2 | 550 |
| 91 | 0.075 | 1-Methylbenzimidazole (10) | $Rh(CO)_2$ acetylacetonate (0.025) | — | Tetraglyme | 240 | 2 | 550 |
| 92 | 0.30 | Imidazole (8) | $Rh(CO)_2$ acetylacetonate (0.1) | 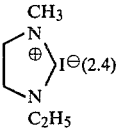 (2.4) | Tetraglyme | 200 | 2 | 550 |
| 93 | 0.30 | Imidazole (8) | $Rh(CO)_2$ acetylacetonate (0.1) | 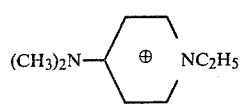 $I^{\ominus}$ (2.4) | Tetraglyme | 200 | 2 | 550 |

TABLE 7-continued

| Example | Methanol | Methyl formate | Ethanol | Methyl acetate | Ethylene glycol | 1,2-Propanediol |
|---|---|---|---|---|---|---|
| 91 | 1.9 | 0.1 | 0.1 | — | 3.6 | 0.2 |
| 92 | 6.8 | 0.1 | 0.7 | 0.1 | 5.7 | 0.4 |
| 93 | 12.0 | 0.2 | 0.3 | — | 7.6 | 0.5 |

COMPARATIVE EXAMPLES 1 TO 3

The inside of a 60 ml autoclave was purged with argon. The autoclave was then charged with 0.1 milligram-atom of $Ru_3(CO)_{12}$, 10 ml of N-methylpyrrolidone and 10 millimoles of the additives shown in Table 8, and closed. Thereafter, the same reaction under the same conditions as in Example 1 was carried out. The results are shown in Table 8.

TABLE 8

| Comparative Example | Additive | Methanol | Methyl formate | Ethanol | Methyl acetate | Ethylene glycol | 1,2-Propanediol |
|---|---|---|---|---|---|---|---|
| 1 | — | 1.4 | 0.1 | 0 | 0 | 0 | 0 |
| 2 | 2-Hydroxypyrieine | 1.9 | 0.1 | 0.1> | 0 | 0.1> | 0 |
| 3 | N—methylmorpholine | 2.1 | 0.1 | 0 | 0 | 0.1> | 0 |

EXAMPLE 94

Example 1 was followed except that the amount of imidazole used was changed to 2 millimoles, and the reaction time was changed to 1 hour. The results are shown in Table 9.

EXAMPLE 95

Example 3 was followed except that the amount of 1-methylimidazole used was changed to 0.5 millimoles. The results are shown in Table 9.

TABLE 9

| Example | Methanol | Methyl formate | Ethanol | Methyl acetate | Ethylene glycol | 1,2-Propanediol |
|---|---|---|---|---|---|---|
| 94 | 23.0 | 1.2 | — | 0.1 | 0.4 | — |
| 95 | 4.3 | 0.2 | — | 0 | 0.1 | 0 |

EXAMPLE 96

The inside of a 38 ml stainless autoclave was purged with argon. The autoclave was then charged with 0.3 milligram-atom of $Ru_3(CO)_{12}$, 1.5 millimoles of imidazole and 7.5 ml of sulfolane and closed. A mixture of carbon monoxide and hydrogen in a molar ratio of 1:1 was introduced into the autoclave through a gas introducing tube until the pressure of the reaction system reached 200 kg/cm². Then, the mixture was heated to 200° C. The pressure of the reaction system reached 290 kg/cm². The mixture was reacted at 200° C. for 4 hours.

After the reaction, the reaction mixture was cooled to room temperature, and after discharging the excess gas, withdrawn.

The reaction mixture was quantitatively determined by gas chromatography, and the results are shown in Table 10.

EXAMPLES 97 TO 99

Example 96 was followed except that the amount of imidazole was changed or the type of the imidazole compound was changed. The results are also shown in Table 10.

COMPARATIVE EXAMPLES 4 TO 6

Example 96 was followed except that 2-hydroxypyridine or purine was used instead of imidazole. The results are also shown in Table 10.

TABLE 10

| Run | | Catalyst Additive | Amount (millimoles) | Methanol | Methyl formate | Ethanol | Methyl acetate | Ethylene glycol | 1,2-Propanediol |
|---|---|---|---|---|---|---|---|---|---|
| Example | 96 | Imidazole | 1.5 | 2.82 | 0.19 | 0 | 0 | 0.21 | — |
| | 97 | Imidazole | 15.0 | 4.97 | 0.16 | 0 | 0 | 0.21 | 0.3 |
| | 98 | 1-Methylimidazole | 1.6 | 1.84 | 0.09 | 0 | 0 | 0.16 | 0 |
| | 99 | Benzimidazole | 1.5 | 1.06 | 0.04 | 0 | 0 | 0.04 | 0.01 |
| Comparative Example | 4 | 2-Hydroxypyridine | 1.5 | 0.07 | 0 | 0 | 0 | 0 | 0 |
| | 5 | 2-Hydroxypyridine | 15.0 | 0.08 | 0 | 0 | 0 | 0.003 | 0 |
| | 6 | Purine | 2.2 | 0 | 0 | 0 | 0 | 0 | 0 |

What we claim is:

1. A process for producing an oxygen-containing organic compound which comprises reacting carbon monoxide with hydrogen in the presence of a catalyst under heat and pressure, said catalyst comprising (a) a ruthenium compound and (b) an imidazole compound represented by the following formula:

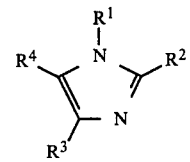

wherein $R^1$ represents a hydrogen atom or a monovalent substituent; $R^2$, $R^3$ and $R^4$ are identical or different, and each represents a member selected from the group consisting of a hydrogen atom, a halogen atom, an alkyl-substituted silyl group and an unsubstituted or substituted hydrocarbon group; or $R^1$ and $R^2$, $R^3$ and $R^4$, or $R^1$ and $R^4$ may be taken together to form a substituted or unsubstituted hydrocarbon group.

2. The process of claim 1 wherein said catalyst contains $10^{-1}$ to $10^7$ moles of the imidazole compound (b) per gram-atom of ruthenium in the ruthenium compound (a).

3. The process of claim 1 or 2 wherein the ruthenium compound (a) is a halogen compound, carboxylate salt, inorganic acid salt, oxide or complex of ruthenium.

4. The process of claim 1 or 2 wherein the ruthenium compound (a) is a carbonyl complex of ruthenium.

5. The process of claim 1 wherein the imidazole compound (b) is a compound represented by the following formula:

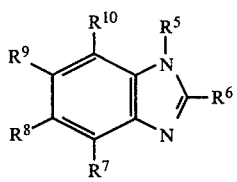

wherein $R^5$, $R^7$, $R^8$, $R^9$ and $R^{10}$ are identical or different and and each represents a hydrogen atom or a monovalent substituent; $R^6$ represents a member selected from the group consisting of a hydrogen atom, a halogen atom, an alkyl-substituted silyl group and un unsubstituted or substituted hydrocarbon group; or $R^5$ and $R^{10}$, $R^5$ and $R^6$, $R^7$ and $R^8$, $R^8$ and $R^9$, or $R^9$ and $R^{10}$ may be taken together to form a substituted or unsubstituted hydrocarbon group.

6. The process of claim 1 wherein the oxygen-containing organic compound is an alcohol having 1 to 3 carbon atoms, a carboxylic acid having 1 to 3 carbon atoms, or an ester of the alcohol and the carboxylic acid.

7. The process of claim 7 wherein the alcohol having 1 to 3 carbon atoms is methanol, ethanol, ethylene glycol, 1,2-propanediol, or glycerol.

8. The process of claim 7 wherein the carboxylic acid having 1 to 3 carbon atoms is formic acid, acetic acid or propionic acid.

9. The process of claim 7 wherein the ester is methyl formate, methyl acetate, ethylene glycol monoformate or ethylene glycol monoacetate.

10. The process of claim 1 or 7 wherein the oxygen-containing organic compound is ethylene glycol.

11. A process for producing an oxygen-containing organic compound which comprises reacting carbon monoxide with hydrogen in the presence of a catalyst under heat and pressure, said catalyst comprising (a) a ruthenium compound and (b) a monoazabenzimidazole compound.

12. The process of claim 11, wherein the monoazabenzimidazole compound is 4-azabenzimidazole.

13. The process of claim 11, wherein the monoazabenzimidazole compound is 1-methyl-4-azabenzimidazole.

* * * * *